United States Patent [19]

Miyano et al.

[11] 4,324,902
[45] Apr. 13, 1982

[54] 7-[5-OXO-3-HYDROXY-2-(3-SUBSTITUTED)-3-HYDROXYPROPYL)-1-CYCLOPENTENE]-HEPTANOIC ACIDS AND DERIVATIVES THEREOF

[75] Inventors: Masateru Miyano, Northbrook; Clifford R. Dorn, Evanston, both of Ill.

[73] Assignee: G. D. Searle & Co., Skokie, Ill.

[21] Appl. No.: 254,828

[22] Filed: Apr. 16, 1981

[51] Int. Cl.$^3$ ............................................. C07C 177/00
[52] U.S. Cl. ........................................ 560/53; 560/60; 560/118; 562/463; 562/470; 562/500; 424/305; 424/308; 424/317
[58] Field of Search ...................... 562/500, 463, 470; 560/118, 53, 60

[56] References Cited

U.S. PATENT DOCUMENTS 4,076,947  2/1978  Schaub et al. ...................... 560/121

*Primary Examiner*—Robert Gerstl

*Attorney, Agent, or Firm*—Daniel J. Long; W. Dennis Drehkoff

[57] ABSTRACT

7-[5-oxo-3-hydroxy-2-(3-substituted)-3-hydroxypropyl)-1-cyclopentene]-heptanoic acids having the following general formula

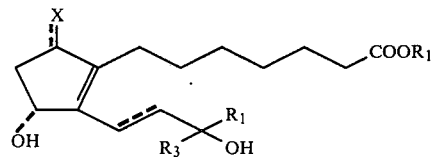

wherein X is oxygen or hydroxyl, $R_1$ and $R_3$ are independently hydrogen or methyl, and $R_2$ is —$(CH_2)_n$-Y where n is an integer from 0 through 4 inclusive, and Y is phenyl, or a cycloalkyl group having 4 to 6 carbon atoms. Said acids as well as certain derivatives thereof are useful as nasal decongestants, inhibitors of gastric secretion, inhibitors of platelet aggregation, blood additives, smooth muscle stimulators, hypotensive agents, labor inducers, and in controlling ovulation.

21 Claims, No Drawings

7-[5-OXO-3-HYDROXY-2-(3-SUBSTITUTED)-3-HYDROXYPROPYL)-1-CYCLOPENTENE]-HEPTANOIC ACIDS AND DERIVATIVES THEREOF

BACKGROUND OF THE INVENTION

1. Field of the Invention

The present invention relates to novel 11,15-dihydroprostenoic acid derivatives and the pharmacologically acceptable salts thereof which are useful as inhibitors of gastric secretion.

2. Description of the Prior Art

U.S. Pat. No. 3,812,172 describes 15-methyl dihydroprostoglandin E (dihydro-PGE), derivatives which are disclosed to be useful as nasal decongestants, inhibitors of gastric secretion, inhibitors of platelet aggregation, blood additives, smooth muscle stimulators, hypotensive agents, labor inducers, and in controlling ovulation.

The compounds of the present invention differ from the compound disclosed in U.S. Pat. No. 3,812,172 in that they are unsaturated between $C_8$ and $C_{12}$ and they have a phenyl or cycloalkyl group attached to C-15 through an alkylene linkage. The compounds of the present invention also differ from prior art compounds in that they do not exhibit the undesirable side effect of smooth muscle stimulation.

SUMMARY OF THE INVENTION

The present invention provides novel 8(12)-prostenoic acid derivatives represented by formula I

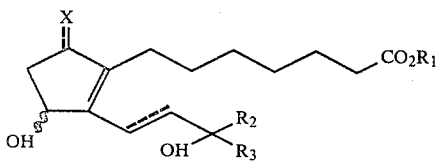

wherein X is oxygen, alpha-hydroxyl or beta-hydroxyl; $R_1$ and $R_3$ may be alike or different and are hydrogen or an alkyl having 1 to 4 carbon atoms; $R_2$ is $-(CH_2)_n-Y$ wherein n is an integer from 0 to 4 inclusive, and Y is phenyl or a cycloalkyl having 4 to 6 carbon atoms; solvates thereof and pharmacologically acceptable salts thereof. When X is oxygen, it is bonded to a carbon atom on the main ring by a double bond, and when X is hydroxyl there is a single bond. The bond between the second and third carbon atoms on the lower side chain may be a single or a double bond.

Compounds of the present invention are useful as anti-secretory agents when administered intravenously in dosages of from 10 μg to 1 mg/kg daily; preferred dosage is from 50 to 100 μg/kg. Preferably the compounds are administered in divided dosages, i.e. 3 to 4 times daily. The compounds can also be administered in such oral unit dosage forms such as tablets, capsules, pills, powders, or granules.

Surprisingly the compounds of this invention are substantially devoid of the undesirable side effect of smooth muscle stimulation.

Each of the novel prostanoic acid derivatives of this invention is encompassed by one of the following formulas or by the combination of that formula and its mirror image:

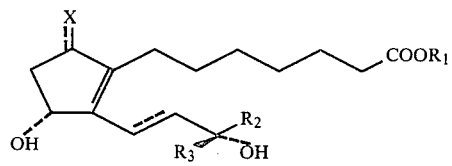

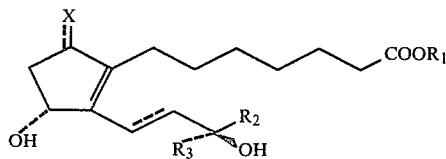

wherein X, $R_1$, $R_2$ and $R_3$ are as defined in formula I.

The terms "alpha-hydroxyl" and "beta-hydroxyl" refer, respectively to the following configurations:

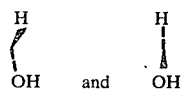

In formula II the configuration of the hydroxyl at $C_{15}$ is S and in formula II the hydroxyl at $C_{15}$ is in the unnatural R configuration. See J. Chem. Education, 41:116 (1964) for a discussion of S and R configuration.

The present invention includes within its scope solvates in which pharmacologicaly insignificant amounts of solvent are present and pharmacologically acceptable salts. Also included within the scope of the invention are intermediates in the preparation of the 8(12)-prostenoic acid derivatives of this invention. Said intermediate compounds include (±)-9,15-dioxo-11-hydroxy-17-phenyl-18,19,20-trisnor-prosta-8(12)-enoic acid methyl ester and (±)-9,15-dioxo-11-hydroxy-17-cyclohexyl-18,19,20-trisnorprosta-8(12), 13 (14)-dien-1-oic acid, and have the following general formula:

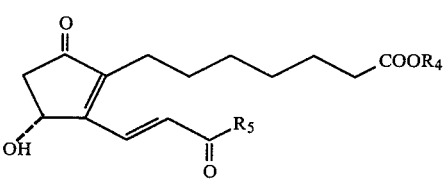

wherein $R_4$ is hydrogen or methyl, $R_5$ is $-(CH_2)-Y$ wherein n is an integer from 0 to 4 inclusive, and Y is a cycloalkyl having 4 to 6 carbon atoms. The solvates and salts of said intermediate compounds are also within the scope of the present invention.

Generally speaking, the compounds of the present invention are conveniently prepared by reacting the appropriate 2-formyl-3-hydroxy-5-substituted cyclopentene-1-heptanoic acid or ester, the preparation of which is described in U.S. Pat. No. 3,932,467, with a substituted carbonylmethylene triphenylphosphorane to give the 15-oxo-11-hydroxy-9-substituted-prosta-8(12),13-dienoic acid or ester. This compound or its silyl ether is reacted with a Grignard reagent to give the corresponding 15-hydroxy-15-alkyl compound which may be reduced to remove the unsaturation at $C_{13}-C_{14}$. The preparation is summarized by the following reaction scheme wherein X, $R_1$, $R_2$ and $R_3$ are defined as above.

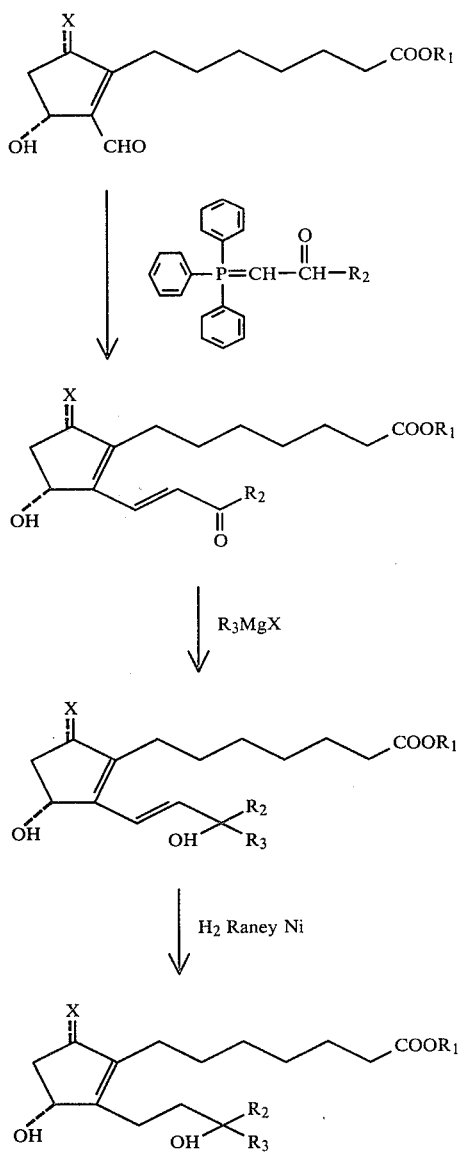

The anti-secretory activity of the compounds of this invention was initially established in the Heidenhain pouch dog assay which evaluates inhibition of gastric secretion stimulated by secretogogues such as histamine and pentogastrin. The specific assay useds to detect gastric antisecretory activity is conducted as follows:

Adult female mongrel dogs weighing 13–20 kg are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1 N sodium hydroxide in pH 7.0. Following a 30 minute basal secretion the dogs are infused with a saline solution of histamine dihydrochloride at a dose of 1.0 mg/hr. The volume of the diffusion is kept at approximately 13 ml/hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

The following examples further illustrate the present invention. These examples are given by way of illustration only and are not to be construed as limiting the invention either in spirit or in scope as many modifications both in materials and in methods will be apparent from this disclosure to those skilled in the art. In these examples, temperatures are given in degrees Centigrade (C°) and quantities of materials in parts by weight unless parts by volume is indicated. The relationship between parts by weight and parts by volume is the same as that existing between grams and milliliters.

EXAMPLE 1

Preparation of (±)-9-oxo-11,15-dihydroxy-17-phenyl-18,19,20-trisnor prost-8(12)-en-1-oic acid methyl ester.

A solution of 475 mg (1.15 mmole) of (±)-9-oxo-11,15-dihydroxy-17-phenyl-18,19,20-trisnor-prosta-8(12),13(14)-dienoic acid methyl ester in 25 ml of dioxane was hydrogenated in the presence of Raney Nickle at atmospheric pressure and room temperature for a period of six hours. The catalyst was removed by filtration and washed with dioxane. The filtrate was concentrated under reduced pressure to give an oil. Low pressure chromatography of the oil on Woelm silica provided (±)-9-oxo-11,15-dihydroxy-17-phenyl-18,19,20-trisnor-prost-8(12)-enoic acid methyl ether which exhibits the following nuclear magnetic resonance spectras: NMR (CDCl$_3$): δ 7.22 (S,5); 4.75 (m,1); 3.70 (m,1); 3.67 (S,3) and is represented by the formula

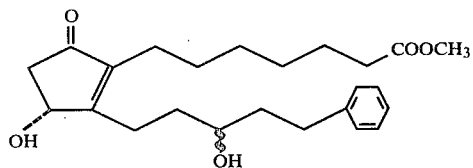

EXAMPLE 2

Preparation of (±)-9-oxo-11,15-dihydroxy-15-methyl-17-phenyl-18,19,20-trisnor-prosta-8(12),-13(14)-dienoic acid. A solution of 4.4 g of (±)9,15-dioxo-11-hydroxy-17-phenyl-prost-8(12),13(14)-dien-1-oic acid in 230 ml of tetrahydrofuran was cooled to −70° C. under a nitrogen atmosphere. A solution of 30 ml of 2.74 M methyl magnesium chloride in tetrahydrofuran was added dropwise with stirring while maintaining the temperature in about −70° C. Stirring was continued at −70° C. for two hours then the mixture was poured onto ice and aqueous citric acid. A small amount of sodium chloride was added and the mixture was extracted twice with ethyl acetate. The combined organic extracts were washed twice with cold, dilute aqueous sodium chloride, dried over anhydrous sodium sulfate, and concentrated under reduced pressure. The residue was purified by low pressure liquid chromatography on silica gel (Silic AR CC-4) using mixtures of methylene chloride-ethyl acetate as eluate to give an oil which was an epimeric mixture of (±)-9-oxo-11,15-dihydroxy-15-methyl-17-phenyl-18,19,20-trisnor-prosta-8(12),13(14)- dienoic acid. This product exhibits the following nuclear magnetic resonance spectra: NMR(CDCl₃): δ 7.20(S,5); 6.67(S,2); 6.22(broad S,2); 5.04(m,1); 1.40(S,3) and is represented by the formula

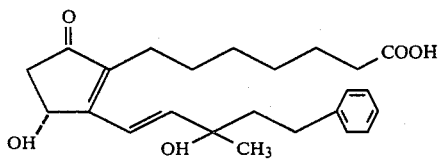

EXAMPLE 3

Preparation of (±)-9,11,15-trihydroxy-15-methyl-17-phenyl-18,19,20-trisnor-prosta-8(12),13(14)-dienoic acid.

A solution of 495 mg (1.2 mmole) of (±)-9-oxo-11,15-dihydroxy-15-methyl-17-phenyl-18,19,20-trisnor-prosta-8(12),13(14)-dien-1-oic acid in 25 parts by volume of tetrahydrofuran is stirred and cooled to −70° C. under a nitrogen atmosphere. A solution of 12 ml of 0.5 M lithium perhydroborophenalyl borohydride in tetrahydrofuran is added dropwise while maintaining a temperature of about −70° C. The solution is held at −70° C. and stirred for 45 minutes then carefully poured into ice water. The mixture is washed twice with ether to remove any neutral material. The aqueous phase is acidified with citric acid and extracted three times with ethyl acetate. The organic solutions are combined, washed 3 times with cold water, dried over anhydrous sodium sulfate, then concentrated under reduced pressure to give an oil. Low pressure liquid chromatography of the oil on Silic AR CC-4 gives (±)-9,11,15-trihydroxy-15-methyl-17-phenyl-18,19,20-trisnor-prosta-8(12),13(14)-dienoic which exhibits the following nuclear magnetic resonance spectra: NMR(CHCl₃) δ 7.22(S,5); 6.28(m2); 4.8–4.2(complex,4); 1.40(S,3) and is represented by the formula

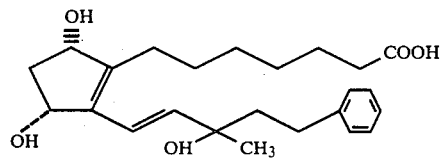

EXAMPLE 4

Preparation of (−)-9,15-dioxo-11-hydroxy-17-cyclohexyl-18,19,20-trisnor-prosta-8(12),13(14)-dienoic acid.

About 25 g of crude (±)-2-formyl-3-hydroxy-5-oxo-1-cyclopentene-1-heptanoic acid is dissolved in 250 ml of tetrahydrofuran acid reacted with 35 g of 3-cyclohexyl-propionyl-methylene(triphenyl)phosphorane. After standing at room temperature for seven days in a stoppered flask the reaction mixture is concentrated under vacuum and the residue is azeotroped with toluene to remove the last traces of tetrahydrofuran. The residue is twice subjected to low pressure chromatography on Silic AR CC-4 silica gel to give (±)-9,15-dioxo-11-hydroxy-17-cyclohexyl-18,19,20-trisnor-prosta-8(12),13(14)-dienoic acid an almost colorless oil exhibiting the following nuclear magnetic resonance spectra: NMR (CHCl₃) δ 7.50(d,1); 7.20(d,1); 5.11(m,1) and represented by the formula

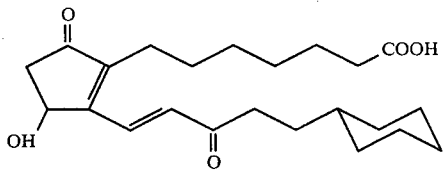

EXAMPLE 5

Preparation of (±)-9-oxo-11,15-dihydroxy-15-methyl-17-cyclohexyl-18,19,20 trisnor-prosta-8(12),13(14)-dien-1-oic acid.

A solution of 3 g of (±)-9,15-dioxo-11-hydroxy-17-cyclohexyl-8(12),13(14)-dien-1-oic acid in 300 ml of tetrahydrofuran is cooled to −70° C. under a nitrogen atmosphere. A solution of 30 ml of 2.5 M methylmagnesium chloride in tetrahydrofuran is added dropwise at −70° C. The reaction mixture is stirred for 90 minutes at −70° C. then poured into ice and aqueous citric acid. The mixture is extracted twice with ethyl acetate. The combined organic solutions are washed with cold, dilute aqueous sodium chloride, dried over anhydrous sodium sulfate, then concantrated to an oil under reduced pressure. This crude product is purified by low pressure liquid chromatography on Silic AR CC-4 silica gel using mixtures of toluene and ethyl acetate as eluant to give an epimeric mixture obtained as an oil which exhibits the following nuclear magnetic resonance spectra: NMR (CDCl₃) δ 6.68(broad S,2); 5.42(broad m,3); 5.10(m,1); 1.38(S,3) and is represented by the formula

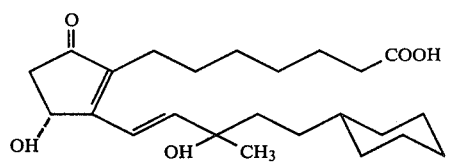

We claim:
1. A compound of the formula

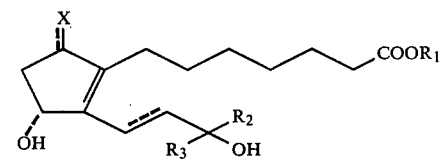

wherein X is oxygen or hydroxyl, $R_1$ and $R_3$ are independently hydrogen or methyl and $R_2$ is —(CH₂)n-Y where n is an integer from 0 through 4 inclusive, and Y is phenyl, or a cycloalkyl group having 4 to 6 carbon atoms, and the pharmacologically acceptable salts thereof.

2. A compound as recited in claim 1 having the formula

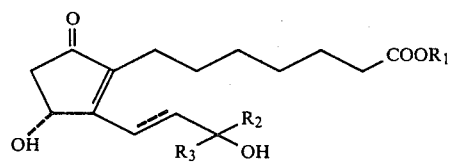

wherein $R_1$ and $R_3$ are independently hydrogen or methyl, and $R_2$ is —$(CH_2)n$-Y where n is an integer from 0 through 4 inclusive, and Y is phenyl, or a cycloalkyl group having 4 to 6 carbon atoms, and the pharmacologically acceptable salts thereof.

3. A compound as recited in claim 2 wherein $R_1$ is methyl.

4. A compound as recited in claim 3 wherein $R_3$ is hydrogen.

5. A compound as recited in claim 4 wherein Y is phenyl.

6. A compound as recited in claim 5 which is 9-oxo-11,15-dihydroxy-17-phenyl-18,19,20-trisnor-prost-8(12)-enoic acid methyl ester.

7. A compound as recited in claim 2 wherein $R_1$ is hydrogen.

8. A compound as recited in claim 7 wherein $R_3$ is methyl.

9. A compound as recited in claim 8 wherein Y is phenyl.

10. A compound as recited in claim 9 which is 9-oxo-11,15-hydroxy-15-methyl-17-phenyl-18,19,20-trisnor-prosta-8(12),13(14)-dienoic acid.

11. A compound as recited in claim 8 wherein Y is cyclohexyl.

12. A compound as recited in claim 8 which is 9-oxo-11,15-dihydroxy-15-methyl-17-cyclohexyl-18,19,20-trisnor-prosta-8(12),13(14)-dienoic acid.

13. A compound as recited in claim 1 having the formula wherein $R_1$ and $R_3$ are independently hydrogen or methyl, and $R_2$ is —$(CH_2)n$-Y where n is an integer from 0 through 4 inclusive, and Y is phenyl, or a cycloalkyl group having 4 to 6 carbon atoms, and the pharmacologically acceptable salts thereof.

14. A compound as recited in claim 13 wherein $R_1$ is hydrogen.

15. A compound as recited in claim 14 wherein $R_3$ is methyl.

16. A compound as recited in claim 15 wherein Y is phenyl.

17. A compound as recited in claim 16 which is 9,11,15-trihydroxy-15-methyl-17-phenyl-18,19,20-trisnor-prosta-8(12),13(14)-dienoic acid.

18. A compound of the formula

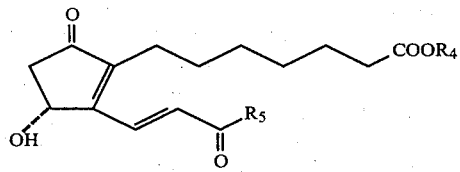

wherein $R_4$ is hydrogen or methyl and $R_5$ is —$(CH_2)n$-Y where n is an integer from 0 to 4 inclusive, and Y is a cycloalkyl having 4 to 6 carbon atoms and the salts thereof.

19. A compound as recited in claim 18 wherein $R_4$ is hydrogen.

20. A compound as recited in claim 19 wherein Y is cycloalkyl.

21. A compound as recited in claim 20 which is 9,15-dioxo-11-hydroxy-17-cyclohexyl-18,19,20-trisnor-prosta-8(12),13(14)-dienoic acid.

* * * * *